United States Patent [19]

Watson

[11] 4,089,859

[45] May 16, 1978

[54] BISQUINOXALINES

[75] Inventor: James M. Watson, Big Spring, Tex.

[73] Assignee: Cosden Technology, Inc., Big Spring, Tex.

[21] Appl. No.: 355,763

[22] Filed: Apr. 30, 1973

[51] Int. Cl.² .......................................... C07D 487/04
[52] U.S. Cl. ............................... 544/353; 260/47 CZ; 260/75 N; 260/78 R; 260/78.41
[58] Field of Search .................................. 260/250 Q

[56] References Cited

U.S. PATENT DOCUMENTS

| 3,637,692 | 1/1972 | Culbertson | 260/250 Q |
| 3,661,850 | 5/1972 | Stille | 260/250 Q |
| 3,804,807 | 4/1974 | Duffy | 260/250 Q |
| 3,887,555 | 6/1975 | Arnold et al. | 260/250 Q |

OTHER PUBLICATIONS

Morrison and Boyd, "Organic Chemistry" 1966, pp. 910–911.

Primary Examiner—Donald G. Daus
Assistant Examiner—David E. Wheeler

[57] ABSTRACT

A composition of matter having the structural formula

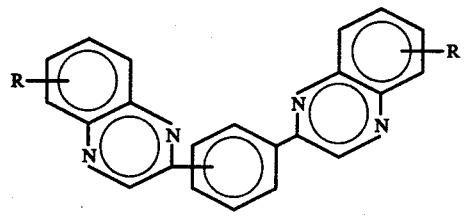

wherein R is a radical selected from the group consisting of carboxylic acid radicals, —OH or —NH$_2$.

4 Claims, No Drawings

BISQUINOXALINES

BACKGROUND OF THE INVENTION

The present invention relates to new and useful organic compounds and to a method for their preparation. More particularly, the present invention relates to quinoxaline compounds and to a process for their manufacture and a method for forming useful polymeric materials from said quinoxaline compounds.

Polyquinoxalines are a group of polymers having excellent heat resistant properties. At least equally important, these polymers are excellent adhesives and are particularly useful s steel-to-steel structural adhesives. The polyquinoxalines presently known generally have heretofore been prepared by reaction of bis(keto-aldehydes) with tetraamines. However, this present method of preparing polyquinoxalines has several disadvantages. One of the disadvantages is that the tetraamines present numerous handling and safety problems, these materials being carcenogenic. Additionally, the tetraamines generally employed to produce these polymers are not readily available and are relatively expensive to obtain. In view of these disadvantages, as well as the general desire to have alternate processes, there is a need for new methods for obtaining the polyquinoxalines.

One potential route to obtaining polyquinoxalines is through the monomeric quinoxalines. However, processes for obtaining monomeric quinoxalines are not well known. Further, there are many possible quinoxaline compounds, many of which have never heretofore been synthesized. Therefore, if the use of monomeric quinoxalines as a source of polyquinoxalines is to find acceptance, there is a need to find new routes to obtaining quinoxaline compounds and a need to find new quinoxaline compounds themselves, which are more suitable as sources of polyquinoxalines.

It is now an object of the present invention to provide a new and novel process for the preparation of quinoxaline compounds.

Another object of the present invention is to provide new and novel compositions of matter.

Still another object of the present invention is to provide a new and novel route to polyquinoxalines.

An additional object of the present invention is to provide new and novel compositions of matter which are bis-quinoxalines.

Yet another object of the present invention is to provide a new and novel process by which bis-quinoxalines may be obtained.

Additional objects will become apparent from the following description of the invention herein disclosed.

SUMMARY OF THE INVENTION

The present invention, which fulfills the above and other objects, is in one of its embodiments a composition of matter comprising bis-quinoxalines having the structural formula

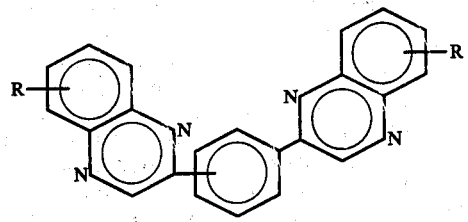

wherein R is a radical selected from the group consisting of carboxylic acid radicals, —OH or —NH$_2$.

In another embodiment, the present invention is a process for the production of bis-quinoxalines having the hereinabove defined structural formula, said process comprising converting diacetylbenzene to the corresponding diglyoxal, and reacting said diglyoxal with a diaminobenzene of the formula

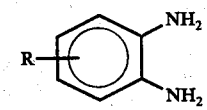

wherein R is a radical selected from the group consisting of carboxyclic acid radicals, —OH and —NH$_2$ to thereby produce said bis-quinoxaline.

In still another embodiment, the present invention is a composition of matter comprising polymer quinoxalines having the structural formula

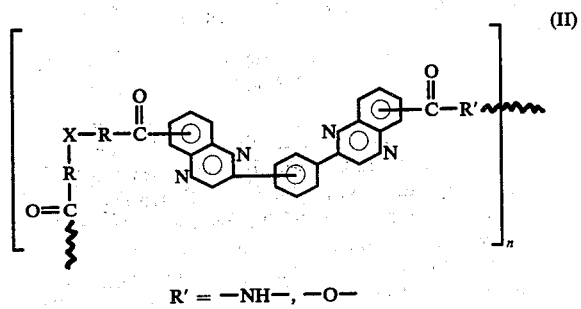

R' = —NH—, —O—

X = alkyl, aryl and

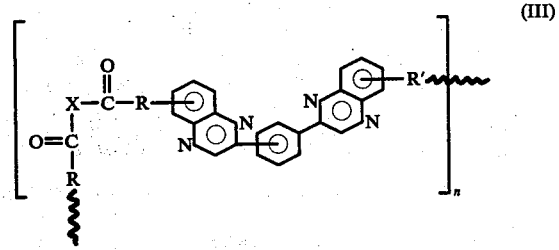

R' = —NH, —O—

X = alkyl, aryl wherein R is a radical selected from the group consisting of —CO$_2$—, —NH and —O— and X is an alkyl or aryl radical and n is an integer of at least 5 and usually no more than 1000.

In still another embodiment, the present invention is a process for the preparation of polyquinoxalines having the above defined structural Formula II and III, said process comprising copolymerizing under polymerization conditions a bis-quinoxaline having the structural Formula (I) above, with a diol or diamine when R in structural Formula (I) is a carboxylic radical, or with a diacid when R is an —OH or —NH$_2$ radical in structural Formula I.

By virtue of the present invention, a new monomeric material is provided which is useful in preparing a new group of useful polymers having good adhesive and high temperature resistant characteristics. Also, a method for the preparation of both the monomers and polymers are provided. By the herein disclosed preparation of the bis-quinoxalines, the use of tetraamines is avoided in the production of the polymeric quinoxalines.

DETAILED DESCRIPTION OF THE INVENTION

In preparing the monomeric bis-quinoxalines of the present invention, a diglyoxal is reacted with certain aminobenzenes. The diglyoxal employed is the derivative of diacetylbenzene and has the formula

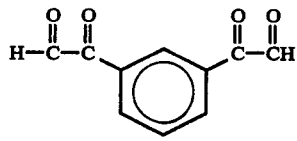

To obtain this diglyoxal from diacetylbenzenes, the diacetylbenzene is oxidized in the presence of a suitable catalyst, preferably one such as selenium dioxide. However, any other catalyst or system which will convert diacetylbenzene to the corresponding diglyoxal may be employed if desired.

The diacetylbenzene used may be any of the three isomeric diacetylbenzens. However, most often the metadiacetylbenzene or the paradiacetylbenzene or mixtures thereof are employed.

In the conversion of the diacetylbenzene to the corresponding diglyoxal employing the above defined preferred catalyst system, the reaction generally is carried out in the presence of a suitable solvent. The solvent should be one inert to the reaction but one in which the reactants may be intimately dispersed. Among the useful solvents are such materials as dioxanes, diphenylether, tetrahydrofuran, benzene, toluene, and the like. The temperatures employed are most frequently within the range of from ambient (20° - 30° C) to 150° C for this reaction. A period of one to 25 hours is most often sufficient for complete conversion of the diacetylbenzene to the corresponding diglyoxal. The diglyoxal product may be recovered from the reaction mixture by filtering and crystallization or any other method desired.

The diglyoxal is reacted with an amino benzene to produce the bis-quinoxalines of the present invention. Among the amino benzenes useful are those diamino benzenes having the formula

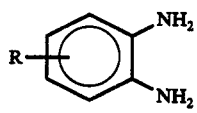

wherein R is a carboxylic acid radical, an —OH or —NH$_2$ radical. When R is a carboxylic acid radical, it preferably is —CO$_2$H. Though it may be any such a radical with any number of carbon atoms, it usually is one with not more than six carbon atoms. In such instance, the carbon atom chain may be either branched or straight chain. The most useful of the diamino benezenes in which R is a carboxylic acid radical are those in which the carboxyclic acid radical contains no more than three carbon atoms.

In the formation of the bis-quinoxalines by reacting the above described diglyoxals with the above defined diamino benzenes in accordance with the present invention, the reactants are employed most often in a ratio of 0.25 to 2.0 mols of diglyoxal per mol of diamino benzene. Preferably, however, this ratio will be within the range of 0.4 to 0.6.

Reaction conditions for the preparation of bis-quinoxalines include a temperature within the range of 40° to 150° C, preferably 60° to 120° C. Pressures are ambient. The reaction preferably is carried out with agitation to insure good contact between the reactants. Usually the contacting or reaction period will be within the range of ½ to 1½ hours, more often, 1 to 1¼ hours. After the reaction is completed, the bis-quinoxalines are removed and purified in accordance with well known techniques. The recovered bis-quinoxalines have the structural Formula (I) hereinabove defined.

The bis-quinoxalines produced as hereinabove described, may be readily converted to polyquinoxalines having a structure in accordance with structural Formula (II) and/or (III) above defined. To produce these polyquinoxalines, the bis-quinoxaline is copolymerized with a diol or a diamine if it contains a carboxyclic acid substituent thereto. If the bis-quinoxaline contains an OH or NH$_2$ substituent in addition to the ortho positioned amino groups, then it preferably is copolymerized with a diacid. Among the useful comonomers for the bis-quinoxalines are the dihydroxybenzenes such as catechol, resorcinol, hydroquinone, ethylene glycol and higher glycols, trihydroxybenzenes, and the like, diamines such as ortho-, meta-, or para-phenylene diamines, hexamethylene diamines and the like, and diacids such as t-phthalic acid, isophthalic acid, phthalic acid, 2,6-naphthalene dicarboxylic acid and the like. The preferred of such comonomers are such compounds as hydroquinone, ethylene glycol and para-phenylene diamine.

In producing the polyquinoxalines, the bis-quinoxalines generally are converted to a polyamide or polyester type polymer. In order to convert the bis-quinoxaline to the corresponding polyamide type of polymer, it generally is preferred to first convert the bis-quinoxaline to the corresponding dihalide which is then copolymerized with a suitable monomer. In a particular useful manner of accomplishing this, the bis-quinoxaline is admixed with an excess of a suitable choride, i.e., thionyl chloride, phospheryl chloride, sulforyl chloride, and the like, and refluxed for three to ten hours. Excess of the chloride is then separated from the mixture and the resulting dichloride dispersed in a suitable solvent, i.e., pyridine, hexamethylphospharamide, dimethyl sulfoxide, dimethylformamide, etc. The dichloride is then admixed with a suitable comonomer such as one of the above mentioned diamines, and permitted to react at a temperature within the range of from ambient temperatures to as high as 100° C and higher. The resulting polymer is precipitated from the mixture and isolated by filtration or other suitable means.

To convert the bis-quinoxaline to a polyester type of polymer, it generally is preferred to convert the bis-quinoxaline to a corresponding ester which is then co-polymerized with suitable diol. In a particular preferred manner of accomplishing this, the bis-quinoxaline is admixed with an excess of methanol in the presence of a few drops of HCl and refluxed for several hours, i.e., three to ten hours. Excess methanol is removed by distillation and the resulting dimethyl ester then brought into intimate contact with an excess of a suitable diol, i.e., ethylene glycol, hydroquinone, and heated at reflux for three to ten hours. The excess diol is removed therefrom leaving a polyester of the bis-quinoxaline.

In order to more fully describe the present invention, the following examples are presented. These examples are not to be construed as limiting of the present invention.

EXAMPLE 1

A mixture comprised of 82 grams (0.74 mol) selenium dioxide, 25 milliliters of $H_2O$ and 500 milliliters of para-dioxane were introduced into a one liter reaction chamber and heated with agitation to 60° C. To this mixture 56.6 grams (0.35 mol) of para-diacetylbenzene was added. The resulting mixture was heated to a reflux temperature of approximately 89° C and maintained at such temperature for about 20 hours. Thereafter, the reaction mixture is filtered and the filter cake reslurried in para-dioxane and again filtered, and then rewashed with additional para-dioxane and water. All of the washings were combined with the original filtrate and the resulting solution concentrated to approximately one-half its original volume and cooled to effect crystallization. The total yield of crude para-phenylenediglyoxaldihydrate was found to be approximately 97% of theoretical.

With 0.67 grams (4.42 millimoles) of 3,4-diaminobenzoic acid was combined 0.5 grams (2.21 millimoles) of the para-phenylenediglyoxal dihydrate prepared above and 10 grams of phenol. This mixture was heated to a temperature of 60° C and then over a period of 1 hour the temperature was gradually raised to 100°. After the end of the one hour period, the reaction mixture was cooled, washed with water and suction filtered to obtain a light brown solid material. This solid material was dried and found to have a melting point of about 400° C. A 96% yield of the crude bis-quinoxaline product was obtained.

The above prepared crude bis-quinoxaline has the following formula:

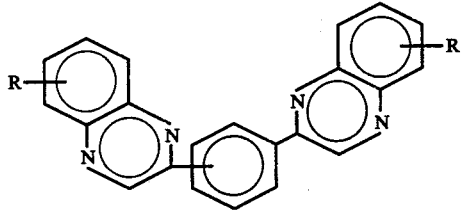

A sample of the product was subjected to microanalysis to determine the carbon, hydrogen and nitrogen percentages therein. The following table provides a comparison of the calculated content of the above defined bis-quinoxaline as compared with that found from the microanalysis.

| Component | Calculated Percent | Percent by Analysis |
| --- | --- | --- |
| Carbon | 68.244 | 66.89 |
| Hydrogen | 3.340 | 3.55 |
| Nitrogen | 13.264 | 12.50 |

EXAMPLE 2

In order to prepare a polyamide type of polymer from a bis-quinoxaline, approximately 422 grams (1 mol) of the bis-quinoxaline prepared above in Example 1 is mixed with an excess (3 mols) of thionyl chloride. This mixture is refluxed for four hours and then the excess thionyl chloride distilled off. The resulting product is the bis-dichloride of the original bis-quinoxaline. This material is dispersed in pyridine. Approximately 1.2 mols of para-phenylenediamine is then added to the reaction mixture and the reaction mixture is permitted to stand at ambient temperture for about 24 hours. After this period of time, the reaction mixture is treated with 3000 grams of methylalcohol to thereby precipitate the polymer. The polymer is collected by filtration. This polymer is found to have good physical properties.

EXAMPLE 3

A bis-quinoxaline of the type produced in Example 1 above is converted to the corresponding polyester type of polyquinoxaline. This is accomplished by mixing 422 grams (1 mol) of the bis-quinoxaline produced in Example 1 above with an excess (3 mols) of methanol and 3 – 5 grams of HCl. This mixture is heated at reflux for five hours and the excess methanol thereafter distilled away. This results in the formation of dimethyl ester of the bis-quinoxaline. This dimethyl ester is then combined with an excess (1.5 mols) of ethylene glycol and heated at reflux for an additional five hours. After the refluxing, the excess glycol is removed by distillation. The resulting material is collected and washed with MeOH for purification. This polymer was found to have good physical properties.

What is claimed is:

1. A compound having the structural formula

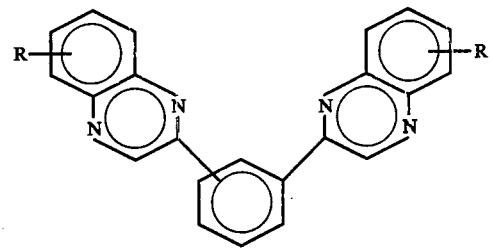

wherein R is selected from the group consisting of a carboxylic acid radical of from 1 to 6 carbon atoms and —OH.

2. The composition of claim 1 wherein R is a carboxylic acid radical of from 1 to 6 carbon atoms.

3. The composition of claim 1 wherein R is —OH.

4. The composition of claim 1, wherein R is —$CO_2H$.

* * * * *